(12) United States Patent
Ikeda

(10) Patent No.: US 7,525,087 B2
(45) Date of Patent: Apr. 28, 2009

(54) METHOD FOR CREATING OBSERVATIONAL SAMPLE

(75) Inventor: Satoshi Ikeda, Tokyo (JP)

(73) Assignee: Oki Semiconductor Co., Ltd., Tokyo (JP)

(*) Notice: Subject to any disclaimer, the term of this patent is extended or adjusted under 35 U.S.C. 154(b) by 348 days.

(21) Appl. No.: 11/604,268

(22) Filed: Nov. 27, 2006

(65) Prior Publication Data

US 2007/0158566 A1 Jul. 12, 2007

(30) Foreign Application Priority Data

Dec. 6, 2005 (JP) ............................. 2005-351847

(51) Int. Cl.
*G01N 1/28* (2006.01)

(52) U.S. Cl. .................. 250/304; 250/307; 250/311

(58) Field of Classification Search ............... 250/304, 250/307, 311

See application file for complete search history.

(56) References Cited

U.S. PATENT DOCUMENTS

| 6,768,110 B2 * | 7/2004 | Alani ........................ 250/307 |
| 7,180,061 B2 * | 2/2007 | Lu ............................ 250/307 |
| 7,317,188 B2 * | 1/2008 | Zhang et al. ................ 250/307 |

FOREIGN PATENT DOCUMENTS

| JP | 2003-194681 | 7/2003 |
| JP | 3547143 | 7/2004 |

* cited by examiner

*Primary Examiner*—Jack I Berman
(74) *Attorney, Agent, or Firm*—Rabin & Berdo, P.C.

(57) ABSTRACT

According to the present invention, a method for creating a sample for a TEM (Transmission Electron Microscope) observation comprising: forming an observation surface at a specific area of a semiconductor device; forming an amorphous protection film on the observation surface; and thinning a portion of the semiconductor device including at least the protection film.

6 Claims, 5 Drawing Sheets

METHOD FOR CREATING OBSERVATIONAL SAMPLE

CROSS REFERENCE TO RELATED APPLICATION

This application claims the priority of Application No. 2005-351847, filed on Dec. 6, 2005 in Japan, the subject matter of which is incorporated herein by reference.

TECHNICAL FIELD OF THE INVENTION

The present invention relates to a method for creating an observational sample for TEM (Transmission Electron Microscope). Especially, the present invention relates to a method for creating a sample for TEM observation following a SEM (Scanning Electron Microscope) or SIM (Scanning Ion Microscope) observation to a specific surface of a LSI device.

BACKGROUND OF THE INVENTION

According to a TEM (Transmission Electron Microscope), electron beams are applied to a sample and electron beams passed through the sample are magnified to form a TEM image. A TEM sample is formed to have a thickness, for example, of 0.05 to 0.4 µm so that electrons may pass therethrough. According to a STEM (Scanning Transmission Electron Microscope), focused electron beams are scanned over a sample and electron beams passed through the sample are detected to form a STEM image. Both TEM and STEM observations require a sample having a small thickness, which electron beams may pass through. Such observation methods have been utilized in a wide technical field including a semiconductor technology, since TEM and STEM observations provide a high resolution image.

In a semiconductor process, failure portions should be observed and analyzed to discover the cause. The failure of a semiconductor device includes foreign matters, open circuits and short circuits. Such failure portions cause of fabricating defective devices, and profits of manufacturing companies may be reduced. In order to improve the yield rate and reliability of semiconductor devices, observation and analysis is required. TEM observation and STEM observation are major and popular methods to find out failure portions of semiconductor devices. Such TEM and STEM may have analysis function to perform high resolution elementary analysis.

According to analysis using a TEM or STEM, including observation, elementary analysis and measurement, an observation surface (sampling surface) of a semiconductor wafer or semiconductor chip is observed. Such an observation is performed to a horizontal surface and a surface of a cross section. In order to create a cross section sample, a specific portion of a semiconductor device is mechanically exposed and is thin-film process is carried out by polishing and ion-thinning processes. Recently, a specific region of a semiconductor device (chip or wafer) is exposed and shaped to be thinner using FIB (Focused Ion Beam), for example, Ga ion beams having an accelerating energy of 30 kV.

A cross section sample created using FIB is observed by a SIM or SEM. In addition, for detailed analysis, a TEM observation is carried out to the same observation surface. A method described in Japanese Patent Publication 2003-194681A is applied to create a TEM sample, in which a sample is shaped to be thinner and the thin sample is extracted from a subject device by a micro manipulator.

Another method for creating TEM sample is described in Japanese Patent Publication No. 3,547,143, in which a sample is extracted from a subject device by a FIB process and is transferred to a sample holder by a mechanical probe. Then a thin-film process is carried out to the sample put on the sample holder.

When a TEM sample is formed or created using FIB after SIM observation or SEM observation, a material etched by Ga ion beams is deposited on an observation surface. Hereinafter, such a material deposited by an etching process is called "etching deposition". If an etching deposition is deposited on the observation surface, the surface could not be observed by a TEM. An etching deposition can be removed by a FIB process, however, the observation surface would be also etched and removed unfavorably; and therefore, a different observation surface is exposed for the following TEM observation.

OBJECTS OF THE INVENTION

Accordingly, an object of the present invention is to provide a method for creating a TEM sample, with which a TEM observation can be performed clearly.

Additional objects, advantages and novel features of the present invention will be set forth in part in the description that follows, and in part will become apparent to those skilled in the art upon examination of the following or may be learned by practice of the invention. The objects and advantages of the invention may be realized and attained by means of the instrumentalities and combinations particularly pointed out in the appended claims.

SUMMARY OF THE INVENTION

According to a first aspect of the present invention, a method for creating a sample for a TEM (Transmission Electron Microscope) observation comprising:

forming an observation surface at a specific area of a semiconductor device;

forming an amorphous protection film on the observation surface; and thinning a portion of the semiconductor device including at least the protection film.

In the first aspect of the present invention, a cavity may be formed to surround the observation surface before the thinning step. The cavity may be formed by a process using focused ion beams. The thinning step may include a step for removing an deposition put on the protection film so that the protection film is remained. The protection film may be of a carbon film or a silicon oxide film. The protection film may be formed on the observation surface by a deposition process using focused ion beams or electron beams.

According to a second aspect of the present invention, a method for observing a specific surface of a semiconductor device, comprising:

forming an observation surface at a specific area of the semiconductor device;

performing SEM (scanning electron microscope) observation to the observation surface;

forming an amorphous protection film on the observation surface; and performing TEM (Transmission Electron Microscope) observation to the same observation surface.

In the second aspect of the present invention, the protection film may be of a carbon film or a silicon oxide film. The protection film may be formed on the observation surface by a deposition process using focused ion beams or electron beams.

According to a third aspect of the present invention, an observation sample, which is created so that a specific observation surface of a semiconductor device is observed using a TEM (Transmission Electron Microscope) after a SEM (scanning electron microscope) observation, comprises:

an amorphous protection film formed on the observation surface.

In the third aspect of the present invention, the amorphous protection film is formed after the SEM observation is completed. The protection film may be of a carbon film or a silicon oxide film. The protection film is formed to have a thickness that is not lager than one tenth of the total thickness of the observation sample.

According to the present invention. a TEM observation can be performed without obstruction by an etching deposition, which may be put on a surface of a TEM sample in an etching process for creating the TEM sample. As a result, the same observation surface can be clearly observed and analyzed between a SIM (SEM) observation and a TEM observation.

DESCRIPTION OF THE REFERENCE NUMERALS

10: LSI Device
12: Observation Surface
14: Front Area
18: Protection Film
18a: Protection Film (Thin Film)
22: Extension Region
22a: Sample (Thin Film)
24: Rear Area
30: TEM Sample

DETAILED DISCLOSURE OF THE INVENTION

In the following detailed description of the preferred embodiments, reference is made to the accompanying drawings which form a part hereof, and in which is shown by way of illustration specific preferred embodiments in which the inventions may be practiced. These preferred embodiments are described in sufficient detail to enable those skilled in the art to practice the invention, and it is to be understood that other preferred embodiments may be utilized and that logical, mechanical and electrical changes may be made without departing from the spirit and scope of the present inventions. The following detailed description is, therefore, not to be taken in a limiting sense, and scope of the present inventions is defined only by the appended claims.

Figure 1:
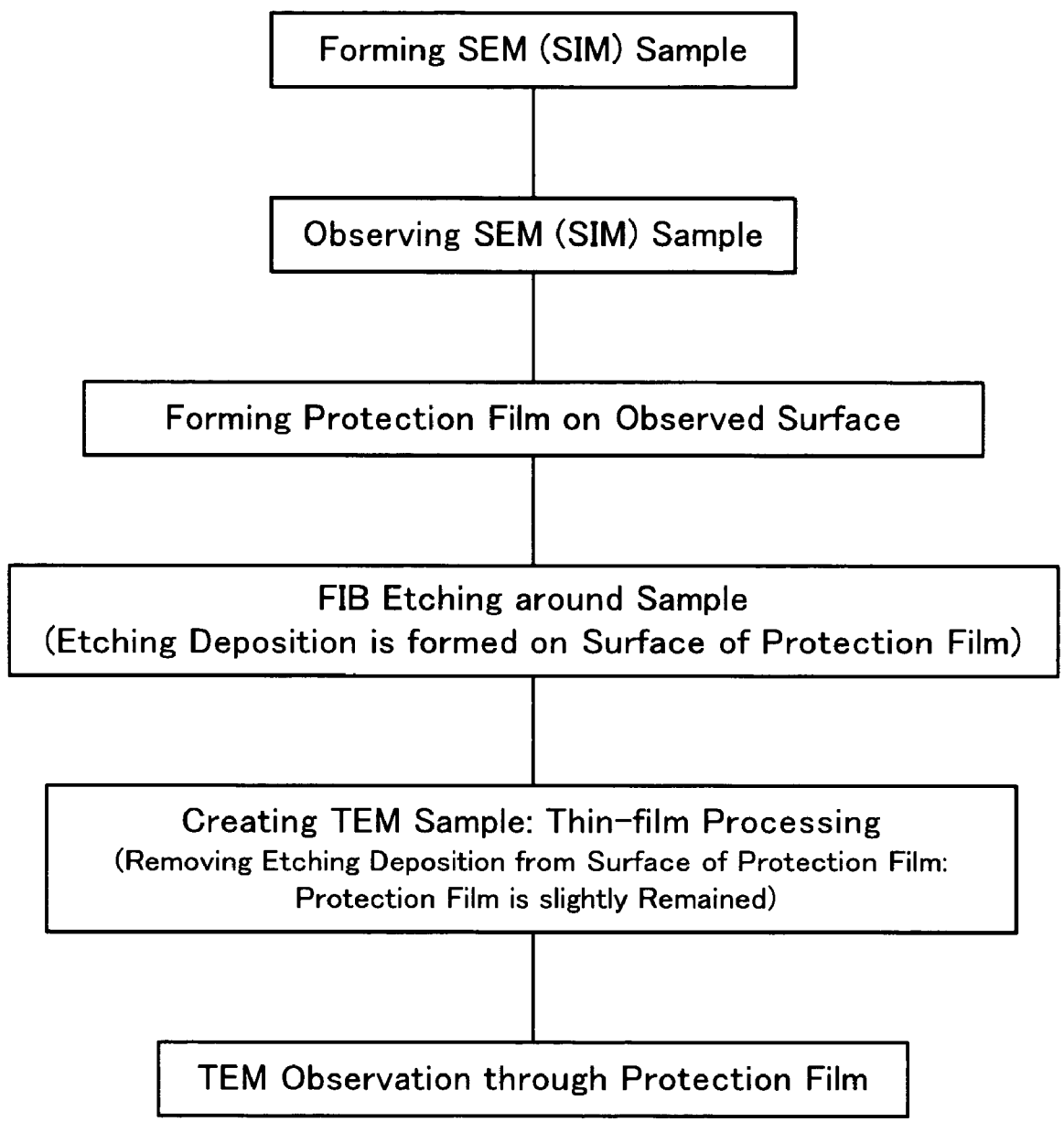
FIG. 1 is a flow chart showing steps for observing a semiconductor device according to a preferred embodiment of the present invention.
Figure 2:
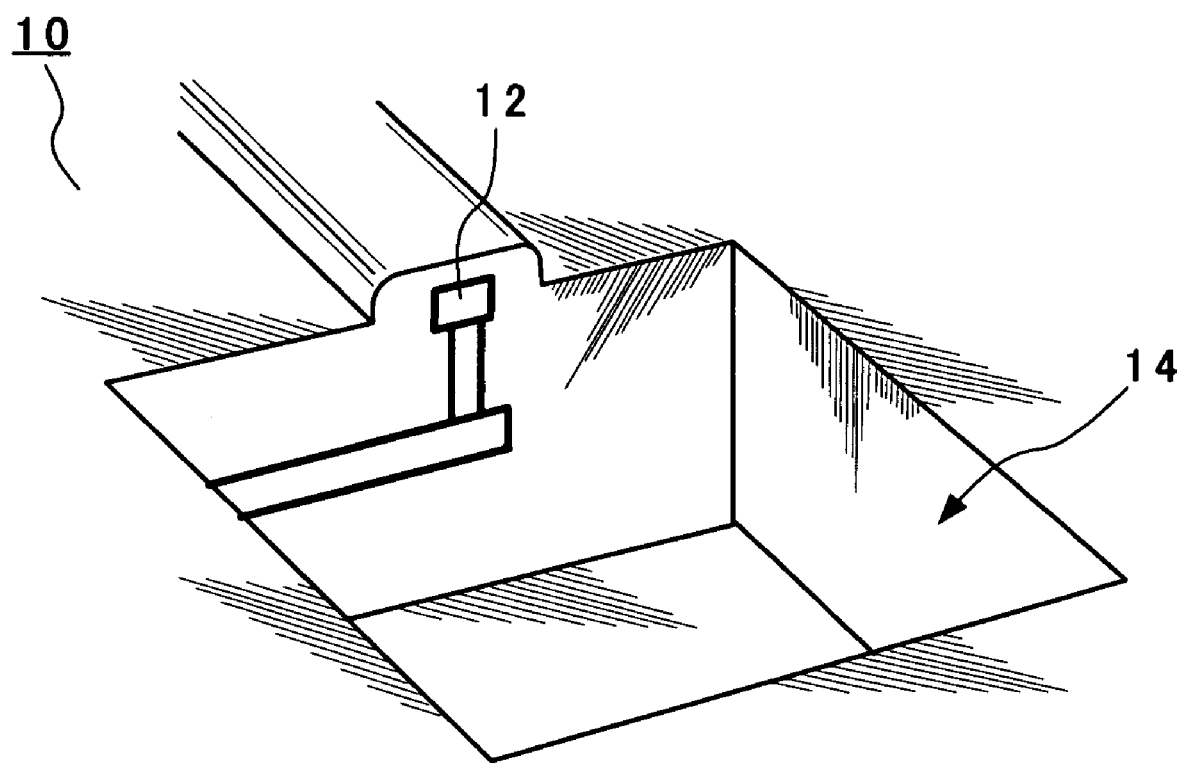
FIG. 2 is a perspective view illustrating an intermediate product of a TEM observation sample according to the preferred embodiment, which includes a surface to be SIM (SEM) observed.

The present invention is now described with an embodiment as follows: FIG. 1 is a flow chart showing steps for observing a semiconductor device according to a preferred embodiment of the present invention. FIGS. 2 to 5 are perspective views each illustrating an intermediate product of a TEM observation sample according to the preferred embodiment. Firstly, as shown in FIG. 2, a specific region of a LSI device 10 is processed with FIB (Focused Ion Beam) technique to form an empty space (room) 14, so that an observation surface 12 is exposed inside the empty space (room) 14. After that, ion beams or electron beams are irradiated to the observation surface 12 to perform SIM (Scanning Ion Microscope) observation or SEM (Scanning Electron Microscope) observation.

Figure 3:
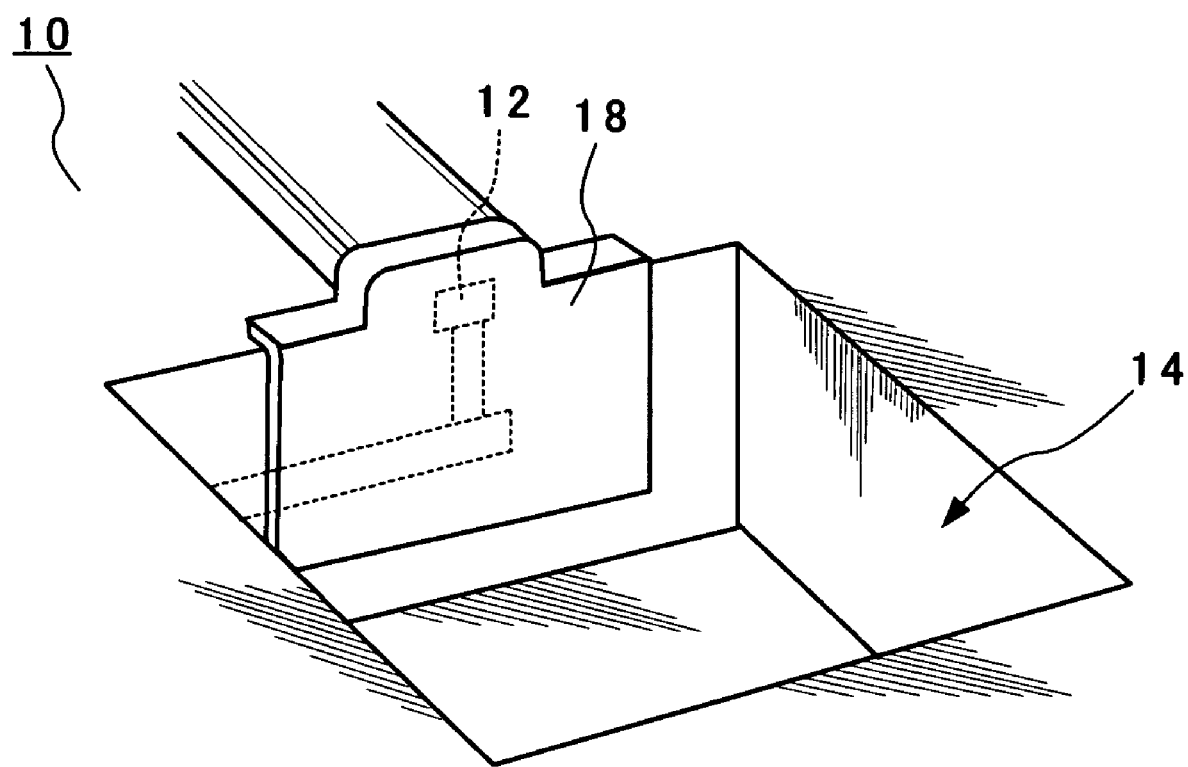
FIG. 3 is a perspective view illustrating an intermediate product of a TEM observation sample according to the preferred embodiment, which includes a surface with a protection film on it.

Next, as shown in FIG. 3, a protection film (layer) 18 is formed (deposited) on the observation surface 12 by focused ion beams using a deposition function of a FIB apparatus. The protection film 18 is a amorphous film. The protection film 18 may be formed by a deposition process using electron beams. The protection film 18 may be of a light element material, having a mass less than that of silicon, for example, carbon and silicon oxide layer. The protection film 18 has a thickness of larger than 100 nm.

Figure 4:
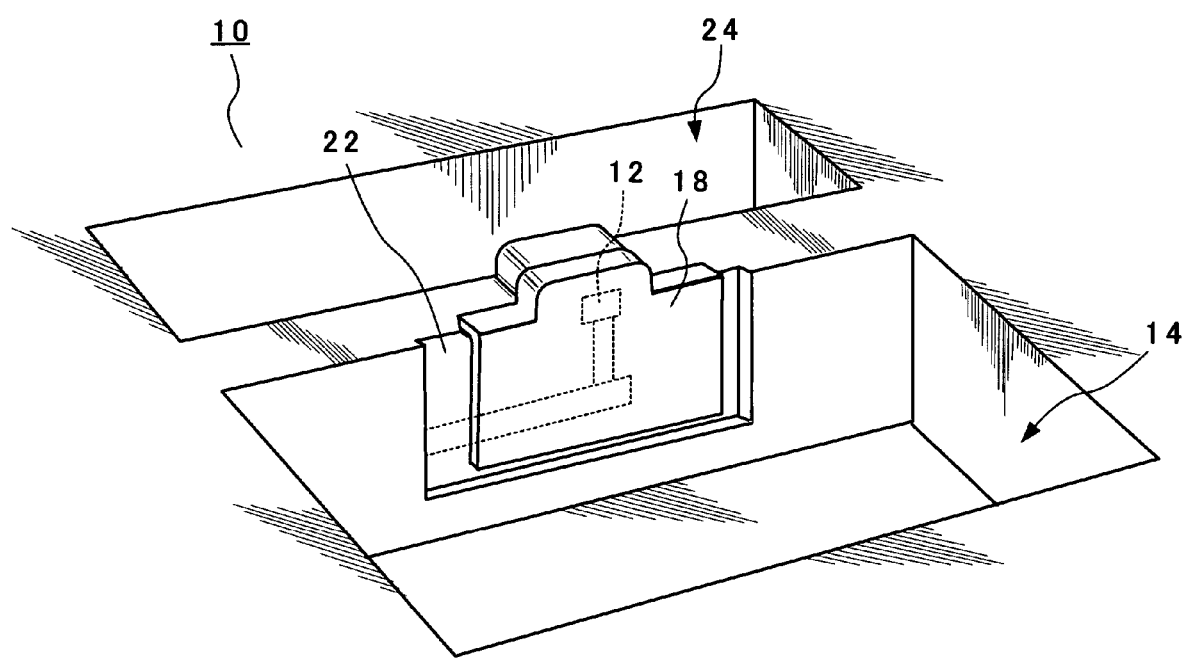
FIG. 4 is a perspective view illustrating an intermediate product of a TEM observation sample according to the preferred embodiment, which includes an etched area surrounding an observation area.

Next, as shown in FIG. 4, a FIB etching is carried out to the device to form a rear space 24 behind the observation surface 12, to extend the front space 14 and to form an extension region 22 surrounding the observation surface 12. The extension region 22 is formed by removing (etching) a surrounding area of the protection film 18. In the etching process, an unfavorable etching deposition may be formed on a surface of the protection film 18. The unfavorable deposition is removed in a FIB etching process, which is carried out for shaping the TEM sample thinner. In such an etching process, the protection film 18 is also etched but is remained slightly.

Figure 5:
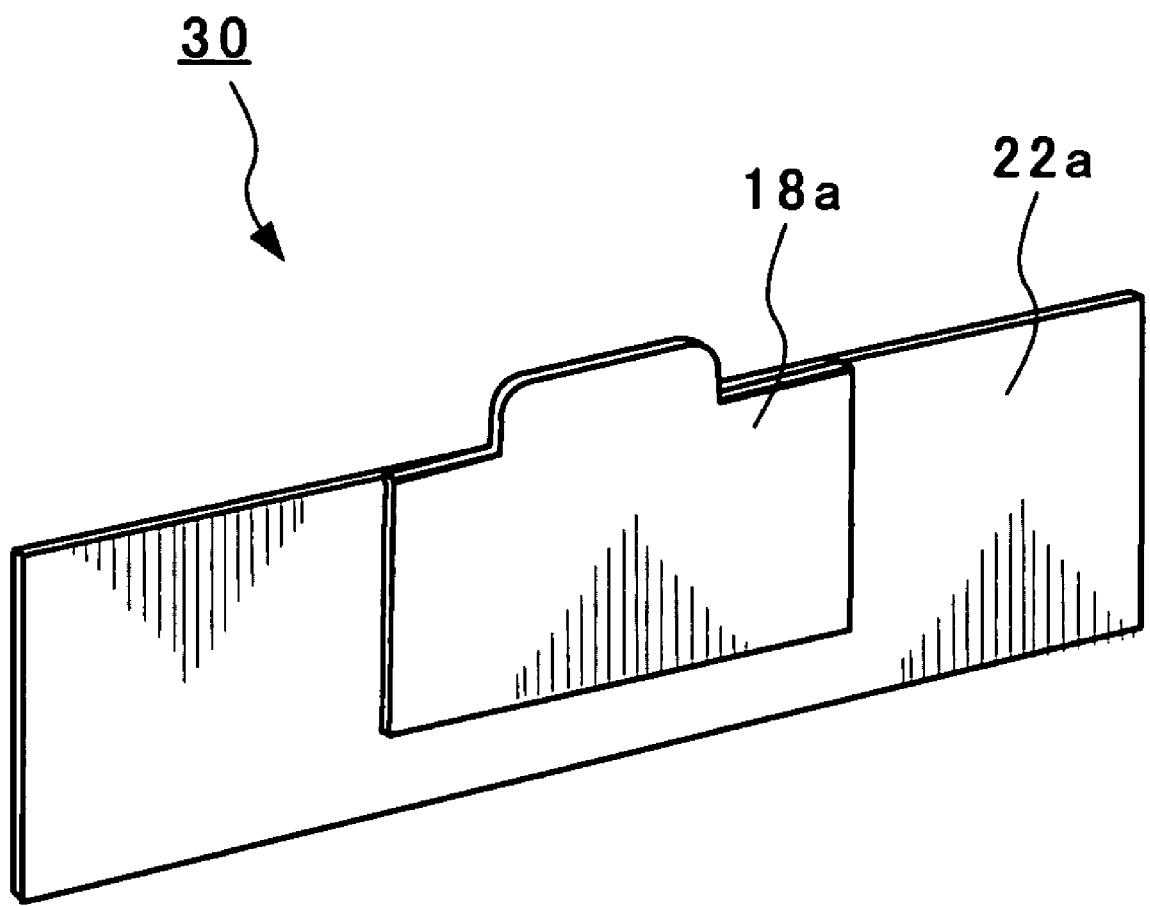
FIG. 5 is a perspective view illustrating a completed TEM observation sample according to the preferred embodiment.

FIG. 5 shows the structure of a TEM sample 30, which has been thin-filmed to include a body portion 22 having a thickness, for example, of 0.1 to 0.15 m. A protection film 18a in a state of after etching preferably has a thickness of less than one tenth of the body portion 22a. After that, a TEM observation is carried out to the sample 30 through the protection film 18a in a well known process.

According to the preferred embodiment, the observation surface 12 is prevented from having an etching deposition on it. That is because; the protection film 18 is formed on the observation surface 12, so that an etching deposition is put only on a surface of the protection film 18. Further, the etching deposition put on the protection film 18 is easily removed without etching the observation surface 12. Although, the protection film 18 is slightly remained on the observation surface 12, a TEM observation can be carried out through the protection film 18, because the protection film 18 (18a) is made of an amorphous material.

What is claimed is:

1. A method for creating a sample for a TEM (Transmission Electron Microscope) observation comprising:

forming an observation surface at a specific area of a semiconductor device;

forming an amorphous protection film on the observation surface; and thinning a portion of the semiconductor device including at least the protection film.

2. A method for creating a sample for a TEM observation according to claim 1, further comprising forming a cavity to surround the observation surface before the thinning step.

3. A method for creating a sample for a TEM observation according to claim 1, wherein the thinning step comprises a step for removing an deposition put on the protection film so that the protection film is remained.

4. A method for creating a sample for a TEM observation according to claim 1, wherein the protection film is of a carbon film or a silicon oxide film.

5. A method for creating a sample for a TEM observation according to claim 1, wherein the protection film is formed on the observation surface by a deposition process using focused ion beams or electron beams.

6. A method for creating a sample for a TEM observation according to claim 2, wherein the cavity surrounding the observation surface is formed by a process using focused ion beams.

* * * * *